(12) United States Patent
Uellner et al.

(10) Patent No.: US 8,636,813 B2
(45) Date of Patent: Jan. 28, 2014

(54) HAIR COLOURING COMPOSITION

(75) Inventors: Martin Uellner, Darmstadt (DE); Alexandra Meuser, Egelsbach (DE); Sandra Schmelz, Marktheidenfeld (DE); Diana Bauer, Darmstadt (DE)

(73) Assignee: Kao Germany, Darmstadt (DE)

( * ) Notice: Subject to any disclaimer, the term of this patent is extended or adjusted under 35 U.S.C. 154(b) by 0 days.

(21) Appl. No.: 13/995,394

(22) PCT Filed: Dec. 23, 2011

(86) PCT No.: PCT/EP2011/073975
§ 371 (c)(1), (2), (4) Date: Jun. 18, 2013

(87) PCT Pub. No.: WO2012/089673
PCT Pub. Date: Jul. 5, 2012

(65) Prior Publication Data
US 2013/0298936 A1      Nov. 14, 2013

(30) Foreign Application Priority Data
Dec. 28, 2010 (EP) .................................. 10016116

(51) Int. Cl.
*A61Q 5/10* (2006.01)

(52) U.S. Cl.
USPC .................. 8/405; 8/406; 8/435; 8/580; 8/696

(58) Field of Classification Search
USPC .............................. 8/405, 406, 435, 580, 696
See application file for complete search history.

(56) References Cited

U.S. PATENT DOCUMENTS

2010/0257677 A1* 10/2010 Miyabe et al. .................... 8/405

FOREIGN PATENT DOCUMENTS

| DE | 44 30 522 A1 | 2/1996 |
|---|---|---|
| EP | 0 928 608 A2 | 7/1999 |
| EP | 1 291 006 A1 | 3/2003 |
| EP | 2 204 160 A1 | 7/2010 |

OTHER PUBLICATIONS

International Search Report mailed Dec. 13, 2012.

* cited by examiner

*Primary Examiner* — Eisa Elhilo
(74) *Attorney, Agent, or Firm* — Norris McLaughlin & Marcus PA

(57) ABSTRACT

Present invention relates to a dyeing composition for hair with improved dyeing and conditioning properties of hair. The object of the present invention a composition for dyeing hair based on at least one hair dye and comprising at least one amino acid surfactant and at least one natural oil.

14 Claims, No Drawings

HAIR COLOURING COMPOSITION

This application is a 371 application of PCT/EP2011/073975 filed Dec. 23, 2011, which claims foreign priority benefit under 35 U.S.C. §119 of European Application No. 10016116.5 filed Dec. 28, 2010.

Present invention relates to a dyeing composition for hair with improved dyeing and conditioning properties of hair.

Dyeing is a common in hair dressing practice. Various dyeing compositions have been made available on the market either based on new dyestuffs with improved dyeing effects and/or giving possibility in achieving new colours or based on non-dyeing chemicals for better uptake of the dyestuffs and for leaving hair in a good condition. Despite the developments, there is still need for further improvements especially in reducing hair damage and leaving hair in a cosmetically acceptable status so that no additional composition for improving cosmetic properties of hair has to be used subsequently. It has especially been observed that multiple processed hair and hair including parts with various degree of damage is difficult to dye homogeneously and also gives problems in their cosmetic properties after dyeing. Hair cosmetic properties referred to are especially combability, elasticity, natural softness and feeling upon touching and bounce.

Based on the above, the aim of the present invention is to provide a dyeing composition with improved dyeing effect on hair and, which, at the same time, colours especially multiple processed hair and hair including parts with various degree of damage homogeneously and which also leaves hair in a cosmetically improved condition so that no additional composition must be used subsequently.

The inventors of the present invention have surprisingly found out that a composition based on at least one hair dye and comprising further at least one amino acid surfactant and at least one natural oil colours hair homogeneously and leaves hair in an excellently cosmetically acceptable status. It has especially been observed that composition of the present invention colours multiple processed hair and especially the hair including parts with various degree of damage homogeneously and leaves said hair in an excellently cosmetically acceptable condition. It has furthermore observed that with the dyeing compositions of the present invention long lasting colours are achieved which clearly means that colours achieved are stable to environmental influences such as light and washing.

Accordingly the first object of the present invention a composition for dyeing hair based on at least one hair dye and comprising at least one amino acid surfactant and at least one natural oil. Preferably the compositions of the present invention are aqueous compositions and comprise at least 40%, more preferably 50%, most preferably 60% and in particular 70% by weight water, calculated to total of the composition. In a further preferred embodiment of the present invention is at least one amino acid surfactant is an anionic surfactant.

The second object of the present invention is the use of dyeing composition of the present invention for dyeing and conditioning hair homogeneously.

The third object of the present invention is the process for dyeing hair wherein a composition of the present invention is applied onto hair and processed for 1 to 45 min and rinsed off from hair.

The fourth object of the present invention is a process for dyeing hair wherein a composition of the present invention is mixed with a composition comprising at least oxidizing agent immediately before use and applied onto hair and after processing 1 to 45 min rinsed off from hair.

The composition of the present invention is provided to the consumers preferably in kit and therefore further object of the present invention is a kit for dyeing hair comprising at least two compositions wherein one of the compositions is according to the present invention and the other is preferably an aqueous composition comprising at least one oxidizing agent.

Composition of the present invention comprises at least one hair dye which is selected from oxidative dyes and direct dyes which may be cationic, anionic and neutral. It should be noted that the direct and oxidative dyes are also suitably used in mixture.

In principal all oxidative dyes available for hair colouring purposes are suitable within the meaning of the present invention. Special mention is made of p-phenylenediamine, p-aminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)amino-benzene, 2-(2-hydroxyethyl amino)-5-aminotoluene, 4,4'-diamino-diphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable ones aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethylpyridine, 2-amino-3-hydroxypyridine, 3-amino-2(β-hydroxyethyl amino)-6-methoxy-pyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof.

Within the meaning of the present invention above mentioned developers can as well be present as a mixture with each other.

The total concentration of the dye precursors (developing substances) customarily ranges between 0.001 to 5%, preferably 0.01 to 4% and more preferably 0.05 to 3%, and most preferably 0.1 to 2% by weight, calculated to the total composition, whereby these figures are always related to the proportion of free base.

In a further embodiment of the present invention compositions comprise in addition to at least one oxidative dye precursor at least one coupling substance. As a rule any coupling substance customarily used in oxidative hair colouration area is suitable within the meaning of the present invention. Non-limiting coupling substances, are 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hydroxyethylamino)benzene, 1-amino-3-[bis(2'-hydroxy-ethyl)amino]benzene, a-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene and/or 1,3-bis(2,4-diaminophenoxy) propane or the water-soluble salts thereof. One or more of the above mentioned coupler can also be used in a mixture.

In the hair dyeing compositions according to the invention, the coupling substance(s) as reaction partners of the developing substance(s) are present in approximately the same molecular proportions as the developing substances, i.e. in amounts from 0.001 to 5%, preferably 0.01 to 4% and more preferably 0.05 to 3%, and most preferably 0.1 to 2% by weight, calculated to the total composition, whereby these figures always relate to the proportion of free base.

Suitable direct dyes are selected from cationic, anionic, neutral dyes and mixtures thereof as available commercially from various suppliers and used mainly in semi-permanent hair coloration.

One of the suitable direct dyes is cationic dyes. Non-limiting examples are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and their salts such as chloride, methosulfate, bromide etc. and mixtures thereof.

Further suitable direct dyes are anionic dyes. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and their mixtures.

Further suitable dyes for colouring hair within the meaning of the present invention are those of neutral nitro dyes. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and their mixtures.

Plant dyestuffs may also be used as hair colorant within the meaning of the present invention for example henna (red or black), alkanna root, laccaic acid, indigo, logwood powder, madder root and rhubarb powder, etc.

It should be noted that the above dyestuffs are also suitably for used in mixture. In other words, cationic, anionic and nitro dyes are used in mixture within the meaning of the present invention. When using direct dyes of various categories, their compatibility must be taken into account.

Among the direct dyes cationic and nitro dyes are preferred ones. Most preferred ones are cationic direct dyes.

Concentration of direct dyes in the compositions of the present invention is within the range of 0.001 to 5%, preferably 0.01 to 4% and more preferably 0.05 to 3%, and most preferably 0.1 to 2% by weight, calculated to total composition.

The total concentration of hair dye is preferably in the range of 0.001 to 15%, preferably 0.01 to 10% and more preferably 0.05 to 7.5%, and most preferably 0.1 to 5% by weight, calculated to total composition.

Composition of the present invention comprises at least one amino acid surfactant. Preferably at least one amino acid surfactant is an anionic surfactant and selected from the ones according to the general structure

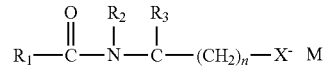

wherein $R_1$ is a saturated or unsaturated, straight or branched alkyl chain with 7 to 17 C atoms, $R_2$ is H or a methyl, $R_3$ is H, $COO^-M^+$, $CH_2COO^-M$ or $COOH$, n is 0 to 2, X is $COO^-$ or $SO_3^-$ and M is independent from each other H, sodium, potassium or ammonium.

With the term amino acid surfactants especially those surfactants are meant derived from taurate, glutamate, alanin or alaninate, sarcosinate and aspartate.

Suitably amino acid surfactant types are taurate, glutamate, alanin or alaninate, sarcosinate, aspartate surfactants, and mixtures thereof. Preferred are taurate, glutamate and sarcosinate surfactants and mixtures thereof. More preferred are taurates and glutamates and especially preferred are glutamate type surfactants.

Suitable taurate surfactants are according to the general formula

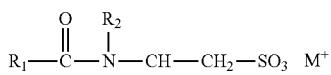

wherein $R_1$ is preferably a saturated or unsaturated, straight or branched alkyl chain with 7 to 17 C atoms, and more preferably 9 to 13 C atoms, $R_2$ is H or methyl, and M is H, sodium or potassium. Suitable examples are potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, and sodium methyl stearoyl taurate and mixtures thereof. Preferred are potassium cocoyl taurate, potassium methyl cocoyl taurate, sodium caproyl methyl taurate, sodium cocoyl taurate, sodium lauroyl taurate, sodium methyl cocoyl taurate and sodium methyl lauroyl taurate and mixtures thereof. More preferred are potassium cocoyl taurate, potassium methyl cocoyl taurate, sodium cocoyl taurate, sodium lauroyl taurate, sodium methyl cocoyl taurate and sodium methyl lauroyl taurate and mixtures thereof.

Suitable glutamate surfactants which are at the same time especially preferred are according to the general formula

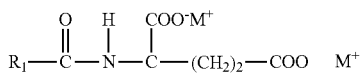

wherein $R_1$ is preferably a saturated or unsaturated, straight or branched alkyl chain with 7 to 17 C atoms, and more preferably 9 to 13 C atoms, and M is independent from each other H, ammonium, sodium or potassium. Suitable examples are dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, and sodium undecylenoyl glutamate and mixtures thereof. Preferred are disodium capryloyl glutamate, disodium cocoyl glutamate, disodium lauroyl glutamate, potassium capryloyl glutamate, potassium cocoyl glutamate, potassium lauroyl glutamate, potassium myristoyl glutamate, sodium capryloyl glutamate, sodium cocoyl glutamate, sodium lauroyl glutamate, and sodium myristoyl glutamate and mixtures thereof. More preferred are disodium capryloyl glutamate, disodium cocoyl glutamate, disodium lauroyl glutamate, potassium capryloyl glutamate, potassium cocoyl glutamate, potassium lauroyl glutamate, sodium capryloyl glutamate, sodium cocoyl glutamate, and sodium lauroyl glutamate and mixtures thereof. Sodium cocoyl glutamate and/or Sodium lauroyl glutamate is especially preferred.

Suitable alanine or alaninate surfactants are according to the general formula

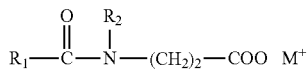

wherein $R_1$ is preferably a saturated or unsaturated, straight or branched alkyl chain with 7 to 17 C atoms, and more preferably 9 to 13 C atoms, $R_2$ is H or methyl and M is H, sodium or potassium. Suitable examples are cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine and sodium myristoyl methyl β-alanine and mixtures thereof.

Suitable glycine surfactants are according to the general formula

wherein $R_1$ is preferably a saturated or unsaturated, straight or branched alkyl chain with 7 to 17 C atoms, and more preferably 9 to 13 C atoms, and M is H, sodium or potassium. Suitable examples are palmitoyl glycine, sodium lauroyl glycine, sodium cocoyl glycine, sodium myristoyl glycine, potassium lauroyl glycine, and potassium cocoyl glycine and mixtures thereof.

Suitable sarcosinate surfactants are according to the general formula

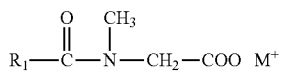

wherein $R_1$ is preferably a saturated or unsaturated, straight or branched alkyl chain with 7 to 17 C atoms, and more preferably 9 to 13 C atoms, and M is H, sodium or potassium. Suitable examples are potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof. Preferred are potassium lauroyl sarcosinate, potassium cocoyl sarcosinate, sodium cocoyl sarcosinate, and sodium lauroyl sarcosinate and mixtures thereof. More preferred are sodium cocoyl sarcosinate, and sodium lauroyl sarcosinate and mixtures thereof.

Suitable aspartate surfactants are according to the general formula

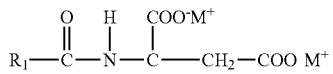

wherein $R_1$ is preferably a saturated or unsaturated, straight or branched alkyl chain with 7 to 17 C atoms, and more preferably 9 to 13 C atoms, and M is independent from each other H, sodium or potassium. Suitable examples are sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, and dipotassium caproyl aspartate and mixtures thereof. Preferred are sodium lauroyl aspartate, sodium myristoyl aspartate, sodium cocoyl aspartate, and sodium caproyl aspartate and mixtures thereof.

It should be noted that compositions of the present invention can also comprise mixture of several type of amino acid surfactants such as mixture of glutamate and taurate surfactants, or mixture of taurate, glutamate and sarcosinate surfactants etc.

In a preferred embodiment of the present invention amino acid surfactants are selected from surfactants comprising at least one carboxyl group and more preferably selected from glutamate, glycine, sarcosinate surfactnts. Particularly preferred is glutamate surfactant.

Concentration of at least one amino acid surfactant in the compositions of the present invention is in the range of 0.05 to 5%, preferably 0.1 to 4% and more preferably 0.1 to 3% and most preferably 0.2 to 2.5% by weight calculated to total of the composition.

Composition of the present invention comprises at least one natural oil. Suitable non-limiting examples are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil. Preferred are argan oil, shea butter oil, karite oil, olive oil, almond oil, avocado oil, ricinus oil, coconut oil, palm oil, sesame oil, peanut oil, whale oil, sunflower oil, peach kernel oil, wheat germ oil, macadamia nut oil, macadamia oil, night primrose oil, jojoba oil, castor oil, and soya oil. More preferred are argan oil, shea butter oil, karite oil, macadamia nut oil, macadamia oil, olive oil, almond oil, avocado oil, ricinus oil, coconut oil, palm oil, sesame oil, peanut oil, sunflower oil, peach kernel oil, wheatgerm oil, jojoba oil, castor oil, and soya oil. Most preferred are argan oil, shea butter oil, karite oil, olive oil, almond oil, avocado oil, coconut oil, macadamia nut oil, macadamia oil, palm oil, sesame oil, peach kernel oil, wheatgerm oil, jojoba oil, and soya oil. Particularly preferred are argan oil and shea butter oil. karite oil which may be comprised as a single oil component or in admixture with each other.

Concentration of at least one natural oil is in the range of 0.01 to 5%, preferably 0.02 to 4%, more preferably 0.05 to 2.5% and most preferably 0.1 to 1.5% by weight calculated to total composition.

pH of the compositions vary in the range of 2 to 12, preferably 5 to 11, more preferably 6 to 10.5 and more preferably 6.8 to 10.5. In case a high lightening effect is looked for, i.e. lightened hair colour is 3 to 4 levels lighter than original hair colour, that high pH values must be preferred. It is the general knowledge of the skilled worker that at alkaline pH the lightening effect is also higher.

Compositions of the present invention comprises preferably at least one alkalizing agent, preferably selected from ammonia (or ammonium hydroxide) and a compound according to the following general structure

wherein $R_4$, $R_5$ and $R_6$ are same or different H, $C_1$-$C_6$ alkyl, $C_1$-$C_6$ monohydroxyalkyl or $C_2$-$C_6$ polyhydroxyalkyl with the condition that at least one of $R_1$, $R_2$ and $R_3$ is a mono or polyhydroxyalkyl. Composition of the present invention comprises at least one alkalizing agent selected from the compounds according t general structure given above. In the preferred embodiment of the present invention, at least one alkanolamine is selected from compounds according to the above general structure wherein $R_1$, $R_2$ and $R_3$ are same or different H, $C_1$-$C_4$ alkyl, $C_1$-$C_4$ monohydroxyalkyl or $C_2$-$C_4$ polyhydroxyalkyl with the condition that at least one of $R_1$, $R_2$ and $R_3$ is a mono or polyhydroxyalkyl.

According to the most preferred embodiment of the present invention at least one alkanolamine is selected from compounds according to the above general formula wherein $R_1$, $R_2$ and $R_3$ are same or different H, $C_2$-$C_4$ alkyl, $C_2$-$C_4$ monohydroxyalkyl or $C_2$-$C_4$ polyhydroxyalkyl with the condition that at least one of $R_1$, $R_2$ and $R_3$ is a mono or polyhydroxyalkyl.

Suitable alkanolamines according to the general formula of above are monoethanolamine, diethanolamine, triethanolamine, monoethanol methylamine, monoethanoldimethylamine, di-ethanol/methylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine.

The concentration of at least one alkalizing agent in the compositions varies between 1 and 35%, preferably 1 and 30%, more preferably 2.5 and 25% and most preferably 2.5 to 20% by weight calculated to the total composition.

Composition of the present invention preferably comprises at least one oxidizing agent. Suitable oxidizing agents are hydrogen peroxide, urea peroxide, melamin peroxide or perborate salts. The most preferred is hydrogen peroxide. Concentration of at least one oxidizing agent is in the range of 0.1 to 20%, preferably 0.2 to 15%, more preferably 0.5 to 15% and most preferably 1 to 12% by weight, calculated to total of the composition.

Compositions of the present invention preferably comprise at least one thickening agent. Thickening agent may be suitably selected from anionic, cationic, nonionic and amphoteric polymer. Nonionic and anionic polymers are preferred. Nonionic polymers are especially preferred polymers. Suitable ones are xanthan gum, guar gum, cellulose and its derivatives such as hydroxyethyl cellulose.

The concentration of at least one thickening agent in the compositions varies between 0.01 and 2.5%, preferably 0.05 and 2%, more preferably 0.1 and 1.5% and most preferably 0.2 to 1% by weight calculated to the total of the composition.

Compositions according to the present invention can be in the form of emulsion, solution, dispersion, thickened liquid and/or gel. Emulsions are especially preferred.

Composition of present invention can comprise additionally fatty acids with 0 to 3 ethylenic bonds and with fatty acyl chain length of 12 to 22 C atom.

Concentration of the fatty acids can be in the range of 0.1 to 10%, preferably 0.1 to 7.5% and most preferably 0.2 to 5% by weight calculated to the total composition, prior to mixing with oxidizing agent. Non-limiting examples are myristic acid, palmitic acid, behenic acid, sterasic acid, oleic acid, linoleic acid. The most preferred fatty acid is oleic acid.

Composition of the present invention comprises preferaly at least one fatty alcohol or mixture of fatty alcohols with the chain length of 14 to 22 C atoms which may be straight or branched, saturated or unsaturated. Examples to suitable fatty alcohols, without limiting the choice, are myristyl alcohol, cetyl alcohol, stearyl alcohol, behenyl alcohol, oleyl alcohol and cetostearyl alcohol, octyldodecanol. The most preferred is cetostearyl alcohol well known with its trade name Lanette O or as Lanette N in mixture with sodium cetearyl sulfate from Cognis. Total fatty alcohol content should be in the range of 0.1 to 20%, preferably 0.2 and 15%, more preferably 0.5 and 10% and most preferably 0.5 to 7.5% by weight, calculated to total of the composition.

Compositions according to present invention comprises surfactants selected from anionic, amphoteric (or zwiterionic) and/or cationic surfactants as emulsifier or solubilizer. Cationic surfactants are as well used as hair conditioners in the colouring composition. Most preferred are nonionic surfactants.

The preferred non-ionic emulsifiers are ethoxylated fatty alcohols with an alkyl chain of 12 to 24 C atoms and with number of ethoxyl groups of 2 to 50, preferably 10 to 30. Examples are ceteth-20, seteareth-30, palmeth-20, steareth-20, beheneth-20 etc. These compounds are named according to the fatty alcohol they are originating and number of ethoxyl groups is given at the end. These compounds are well known emulsifiers and found in any cosmetic ingredient book.

Further suited nonionic surfactants are, especially in mixture with fatty alcohol ethoxylates, for example, long-chain fatty acid mono- and dialkanolamides, such as coco fatty acid mono- or diethanolamide and myristic fatty acid mono or diethanolamide, stearic acid mono or diethanolamide.

Further nonionic surfactants suited again especially in admixture with fatty alcohol ethoxylates mentioned above are alkyl polyglucosides of the general formula $$R_8\text{---}O\text{---}(R_9O)_n\text{---}Z_x,$$

wherein $R_8$ is an alkyl group with 8 to 18 carbon atoms, $R_9$ is an ethylene or propylene group, Z is a saccharide group with 5 to 6 carbon atoms, n is a number from 0 to 10 and x is a number between 1 and 5.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}C_{18}$—alkyl dimethyl amineoxides such as lauryl dimethyl amineoxide, $C_{12}C_{18}$— alkyl amidopropyl or -ethyl amineoxides, $C_{12}C_{18}$-alkyl di(hydroxyethyl) or (hydroxypropyl)amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Anionic surfactants other than anionic amino acid surfactants may also be comprised in eh compositions of the present invention. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula $$R_{10}\text{---}(C_2H_4O)_n\text{---}O\text{---}CH_2COOX,$$

wherein $R_{10}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula $$R_{10}\text{---}\underset{\underset{O}{\|}}{C}\text{---}\underset{\underset{H}{|}}{N}\text{---}CH_2\text{---}CH_2\text{---}(C_2H_4O)_n\text{---}CH_2COOX$$

wherein $R_{10}$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

It is also possible to use mixtures of several anionic surfactants in a mixture.

An overview of the anionic surfactants suitable for the present invention can furthermore be found in the monography of K. Schrader, "Grundlagen and Rezepturen der Kosmetika", $2^{nd}$ Ed. (1989, Huthig Buchverlag), pp. 595-600 and pp. 683 to 691.

As further surfactant component, the colouring compositions according to the invention can also contain amphoteric or zwitterionic surfactants, for example in an amount from about 0.5% to about 5%, preferably from about 1% to about 2.5% by weight, calculated to the total composition.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Colouring composition can comprise cationic surfactants as emulsifier, solubilizer and/or conditioning ingredients according to the formula, $$R_{14}\text{---}\underset{\underset{R_{11}}{|}}{\overset{\overset{R_{12}}{|}}{N^+}}\text{---}R_{13}\quad X^-$$

where $R_{12}$ is a saturated or unsaturated, branched or non-branched alkyl chain with 8-22 C atoms or $$R_{15}CONH(CH_2)_n$$

where $R_{15}$ is saturated or unsaturated, branched or non-branched alkyl chain with 7-21 C atoms and n has typical value of 1-4 or $$R_{16}COO(CH_2)_n$$

where $R_{16}$ is saturated or unsaturated, branched or non-branched alkyl chain with 7-21 C atoms and n has typical value of 1-4, and $R_{11}$ is unsaturated or saturated, branched or non-branched alkyl chain with 1-22 C atoms or $R_{15}CONH(CH_2)_n$ or $R_{16}COO(CH_2)_n$ where $R_{15}$, $R_{16}$ and n are same as above.

$R_{13}$ and $R_{14}$ are lower alkyl chain with 1 to 4 Carbon atoms, and X is typically chloride, bromide, methosulfate.

Typical examples of those ingredients are cetyl trimethyl ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Form the above mentioned surfactants preferred are non-ionic and anionic surfactants and their mixtures.

Total surfactant concentration of the above mentioned ones and other than amino acid surfactants is in the range of 0.5 to 15%, preferably 1 to 10%, more preferably 1 to 7.5% by weight calculated to total composition prior to mixing with an oxidizing agent.

Composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 2, Polyquaternium 4, Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 67, Polyquaternium 87.

Typical concentration range for any of the cationic conditioners mentioned above can be 0.01-5% by weight, preferably 0.03-2.5% by weight and more preferably 0.05-1.5% by weight.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

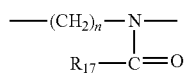

wherein n is a number from 1 to 5 and $R_{17}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

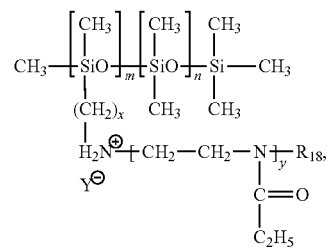

wherein m and n each are numbers from 20 to 10,000, in particular 50 to 7,000, especially 100 to 5,000, x is a number between 1 and 5, preferably 3, and y is a number from 5 to 30, $R_{18}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Compositions according to the present invention can contain organic solvents as penetration enhancers and also as a solubilzers. Examples of such organic solvents are benzyloxy ethanol, benzyl alcohol, phenoxy ethanol, phenoxy isopropanol, methyl phenoxy ethanol, benzyl glycerol, N-benzyl formide, N-methylpyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 20%, preferably 0.5-15%, more preferably 0.5-10%, by weight calculated to the total of the composition.

Compositions may further comprise at least one ubiquinone of the formula

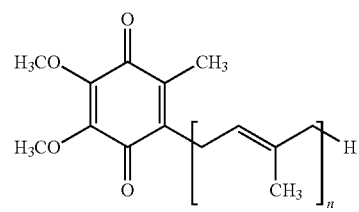

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total of the composition.

The composition comprises ubiquinone which is preferably selected from the ones where n is a number between 6 and 10 and more preferably it is ubiquinone 50 where n is 10, also known as Coenzyme Q10.

Composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition, prior to mixing with oxidizing composition.

Suitable amino acids are glycin, histidine, citrullin, asparagine, alanin, valin, leucin, isoleucin, pyrrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrrolin, serine, tyrosine, threonine and gluatamine. More preferably, at least one amino acid is selected from glycin, histidine, asparagine, alanin, valin, leucin, pyrrolin, serine, tyrosine and gluatamine, and most preferably at least one amino acid is selected from glycin, asparagine, alanin, valin, leucin, and serine.

Composition can comprise further ceramide type of compound with the general formula

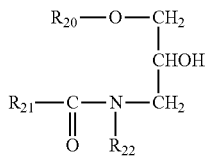

where $R_{20}$ and $R_{21}$ are independent from each other alkyl- or alkenyl group with 10 to 22 carbon atoms, $R_{22}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Following examples are to illustrate the invention but not to limit.

EXAMPLE 1

|  | by weight |
| --- | --- |
| Sodium lauroyl glutamate | 1.0 |
| Argan oil | 0.2 |
| Basic red 51 | 1.0 |
| Monoethanolamine | 5.0 |
| Phosphoric acid/sodium hydroxide | q.s to pH 6.8 |
| Water | q.s. to 100 |

The above composition was prepared by dissolving and mixing the given components in water and pH was adjusted to 6.8.

The above composition coloured human hair homogeneously into an intensive red colour and hair so coloured was well cared in terms combability, shine and softness.

The above composition was added 3% hydrogen peroxide and hair dyed with the obtained composition was homogeneously coloured into a brilliant red and hair was easily combable and softer and shinier.

Additionally pH of the above composition was adjusted to pH 9.5 in the presence of hydrogen peroxide and the above properties of hair were confirmed.

EXAMPLE 2

|  | by weight |
| --- | --- |
| Sodium lauroyl glutamate | 1.0 |
| Argan oil | 0.2 |
| 3,5-diamino-1-hydroxyethyl-pyrazol | 1.0 |
| Resorcinol | 0.5 |
| Monoethanolamine | 5.0 |
| Hydrogen peroxide | 6.0 |
| Phosphoric acid/sodium hydroxide | q.s to pH 6.8 |
| Water | q.s. to 100 |

The above composition was prepared by dissolving and mixing the given components in water and pH was adjusted to 6.8.

It was observed that hair coloured into an intensive homogeneous red color.

EXAMPLE 3

|  | by weight |
| --- | --- |
| Sodium lauroyl glutamate | 1.0 |
| Argan oil | 0.2 |
| 3,5-diamino-1-hydroxyethyl-pyrazol | 1.0 |
| Resorcinol | 0.5 |
| Monoethanolamine | 8.0 |
| Phosphoric acid/sodium hydroxide | q.s to pH 11 |
| Water | q.s. to 100 |

The above composition was mixed with an oxidizing composition comprising 6% hydrogen peroxide at a weight ratio of 1:1. The resulting composition had a pH of 9.6. Hair coloured with the above composition was homogenous in colour, easier to comb and had natural softness. Exclusion of amino acid surfactant and oil resulted in loss of effects and homogenous colouring was also not possible.

EXAMPLE 4

|  | by weight |
| --- | --- |
| Sodium cocoyl glutamate | 1.0 |
| Argan oil | 0.2 |
| Cetearyl alcohol | 5.0 |
| Ceteareth-20 | 2.0 |
| p-toluene dimanine sulphate | 1.0 |
| Resorcinol | 0.5 |
| Monoethanolamine | 5.0 |
| Phosphoric acid/sodium hydroxide | q.s to pH 11.0 |
| Water | q.s. to 100 |

The above composition was mixed with an oxidizing composition comprising 6% hydrogen peroxide at a weight ratio of 1:1. The resulting composition had a pH of 9.8. Hair coloured with the above composition was homogenous in colour, easier to comb and had natural softness. Exclusion of amino acid surfactant and oil resulted in loss of effects and homogenous colouring was also not possible.

The invention claimed is:

1. A composition for dyeing hair comprising at least one hair dye, at least one amino acid surfactant and at least one natural oil wherein at least one amino acid surfactant is selected from anionic surfactants according to general structure

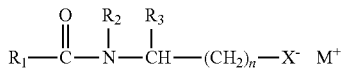

wherein $R_1$ is a saturated or unsaturated, straight or branched alkyl chain with 7 to 17 C atoms, $R_2$ is H or a methyl, $R_3$ is H, $COO^- M^+$, $CH_2COO^- M$ or $COOH$, n is 0 to 2, X is $COO^-$ or $SO_3^-$ and M is independently from each other H, sodium or potassium.

2. The composition according to claim 1 wherein amino acid surfactant is selected from the group consisting of taurate, glutamate, alanin or alaninate, sarcosinate, and aspartate surfactants.

3. The composition according to claim 1 wherein the at least one natural oil is selected from the group consisting of argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil.

4. The composition according to claim 3 wherein the at least one natural oil is argan oil or shea butter oil or karite oil.

5. The composition according to claim 1 wherein the at least one hair dye is an oxidation dye precursor.

6. The composition according to claim 1 wherein the at least one hair dye is a direct dye selected from anionic, cationic and neutral dyes.

7. The composition according claim 1 further comprising at least one alkalizing agent.

8. The composition according to claim 1 wherein the composition has a pH between 2 and 11.

9. The composition according to claim 1 further comprising at least one thickening agent.

10. The composition according to claim 1 further comprising at least one fatty alcohol.

11. The composition according to claim 1 further comprising at least one oxidizing agent.

12. A process for dyeing hair comprising applying a composition according to claim 1 onto hair, processing for 1 to 45 min and rinsing the composition from hair.

13. A process for dyeing hair comprising mixing a composition according to claim 1 with a composition comprising at least oxidizing agent immediately before use, applying the mixtures onto hair processing for 1 to 45 min, and rinsing the mixture from hair.

14. A kit for dyeing hair comprising at least two compositions wherein one of the compositions is according to claim 1 and the other is an aqueous composition comprising at least one oxidizing agent.

* * * * *